US00PP25435P3

(12) United States Plant Patent
Cain

(10) Patent No.: US PP25,435 P3
(45) Date of Patent: Apr. 14, 2015

(54) GRAPEVINE 'IFG SEVENTEEN'

(50) Latin Name: *Vitis vinifera*
Varietal Denomination: IFG Seventeen

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 139 days.

(21) Appl. No.: 13/986,680

(22) Filed: May 24, 2013

(65) Prior Publication Data

US 2014/0352010 P1 Nov. 27, 2014

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Seventeen'. The new grapevine is characterized by producing naturally large, narrow elliptic, black seedless berries which are firm in texture and ripen late in the growing season.

1 Drawing Sheet

Latin name of the genus and species claimed: *Vitis vinifera*. Variety denomination: 'IFG seventeen'.

BACKGROUND OF THE INVENTION

The new and distinct grapevine described and claimed herein originated from a hand pollination of the Autumn Royal variety (USDA non-patented) and bulked pollen derived from several un-named red seedless selections from the Volcani Institute hybridized in May 2001. It is unknown which selection was the actual paternal parent. The abortive seed traces were subsequently embryo cultured and the resulting plant was planted in the field in April 2002. The present variety of grapevine was selected as a single plant in September 2004 and was first asexually propagated by hardwood cuttings in December 2005 near Delano, Kern County, Calif. The resulting propagules were planted during April 2006 at the International Fruit Genetics LLC research facility near Delano, Kern County, Calif. and were found to reproduce true-to-type through at least one generation of asexual reproduction.

BRIEF SUMMARY OF THE INVENTION

The new grapevine 'IFG Seventeen' is characterized by producing naturally large, narrow elliptic, black seedless berries which are firm in texture and ripen late in the growing season. Fruits normally ripen late September to early October near Delano, Calif.

To the inventor's knowledge, the known variety which the new grapevine variety is most similar to is its parent the Autumn Royal variety. 'IFG Seventeen' can be distinguished from the Autumn Royal variety by having a much smaller residual seed trace, by having no tendency to develop an astringent flavor and by having higher, more consistent yields. 'IFG Seventeen' tolerates rain during the ripening season better than the Autumn Royal variety. The canes of 'IFG Seventeen' are more flexible and less brittle than the Autumn Royal variety reducing damage during pruning and other cultural operations. The berries of 'IFG Seventeen' are smaller than the Autumn Royal variety but color more easily.

'IFG Seventeen' can be distinguished from 'IFG Sixteen' by having a more elongated berry and by having a narrower cluster. The Berries of 'IFG Seventeen' are smaller but firmer than 'IFG Sixteen' and they color more easily than 'IFG Sixteen'.

BRIEF DESCRIPTION OF THE FIGURE

The accompanying photographic illustration in FIG. 1 illustrates in full color 'IFG Seventeen'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Seventeen' plants grown in the vicinity of Delano, Kern County, Calif. during 2011 and 2012 and is believed to apply to plants of the variety grown under similar conditions of soil and climate elsewhere:

Vine:

*General.*—Size — Large. Vigor — Vigorous. Density of foliage — Dense. Productivity — Very productive. Root stock — Own root. Training method — Typically spur pruned leaving 2 bud spurs.

*Trunk.*—Trunk diameter of 4-year-old vines at 30 cm above the soil line — 7.6 cm. Shape — Stocky to medium. Straps — Short — split. Surface texture — Medium. Inner bark color — Can be any of the following colors; Greyed orange; 177A and B.

Shoots:

*Young shoot.*—Form of tip — Wide open. Distribution of anthocyanin coloration of tip — Absent. Intensity of anthocyanin coloration of tip — Absent. Density of prostrate hairs of tip — Medium. Density of erect hairs of tip — Absent. Color — Green; 147 A.

*Woody shoot* (*mature canes*).—Shape — Medium thick. Internode length — Short; About 12.0 cm. Width at node — About 1.1 cm. Cross section — Circular. Surface — Striate. Main color — Can be any of the following colors; Greyed orange; 164A and B, and 165A, and 166B. Density of erect hairs of nodes — None. Density of erect hairs on internodes — None. Growth of axillary shoots — Medium to strong; Approximately 36.1 cm.

*Flowering shoot.*—Vigor during flowering — Medium. Attitude during flowering on shoots not tied — Semi-drooping to Drooping. Color — dorsal side of internodes — Green with Red stripes. Color — ventral side of internodes — Green. Color — dorsal side of nodes — Green with Red stripes. Color — ventral side of nodes — Green. Density of prostrate hairs of nodes — Very sparse. Density of erect hairs of nodes — None. Density of prostrate hairs on internode — None. Density of erect hairs on internode — None. Anthocyanin coloration of buds — Absent.

*Tendrils.*—Distribution on the shoot (at full flowering) — Discontinuous. Length of Tendril — Long; About 34.6 cm. Thickness — Thin. Color — Can be any of the following colors; Green; 144A and B and 146A. Form — Can be any of the following; bifurcated and trifurcated and quadfurcated. Number of consecutive tendrils — 1.

Leaves:

*Young leaves.*—Color of upper surface of first four distal unfolded leaves — Reddish green. Average intensity of anthocyanin coloration of six distal leaves prior to flowering — Weak. Density of prostrate hairs between veins (lower surface) — Sparse. Density of prostrate hairs on veins (lower surface) — Sparse to medium. Density of erect hairs between veins (lower surface) — Absent. Density of erect hairs on veins (lower surface) — Sparse.

*Mature leaves.*—Average length — About 16.6 cm. Average width — About 18.8 cm. Mature leaf size — Medium. Shape of blade — Wedge-shaped. Number of lobes — 5. Anthocyanin coloration of main veins on upper side of blade — Weak to medium. Mature leaf profile — V-shaped to involute. Blistering surface of blade upper surface — Weak to medium. Leaf blade tip — In the plane of the leaf. Undulation of margin — Medium. Thickness — Medium. Undulation of blade between main and lateral veins — Overall. Shape of teeth — Mixture of both sides straight and both sides convex. Length of teeth — Medium. Ratio length/width of teeth — Equal. Shape of upper lateral sinuses — Lobes slightly overlapping. Depth of upper lateral sinuses — Very shallow. General shape petiole sinus — Half open. Shape of base of upper leaf sinuses — V-shaped. Tooth at petiole sinus — Absent. Density of prostrate hairs between veins on lower surface of blade — Very sparse. Density of erect hairs between veins on lower surface of blade — Absent. Density of prostrate hairs on main veins on lower surface of blade — Sparse. Density of erect hairs on main veins on lower surface of blade — Sparse. Density of prostrate hairs on main veins on upper surface of blade — Sparse. Density of erect hairs on main veins on upper surface of blade — None. Autumn coloration of leaves — Leaves can be a single color or combination of colors, in a mottled pattern or on the edges of the leaves; Purple N77A, and Greyed purple 187A and B.

*Upper surface.*—Color — Can be any of the following colors; Green; 137A and B and 139A and B. Anthocyanin coloration of main veins — Medium. Surface appearance — Semi-glossy to dull. Blistering surface of blade — Weak to medium.

*Lower surface.*—Color — Can be any of the following colors; Green; 138A and B. Anthocyanin coloration of main veins (lower surface) — Weak. Glossiness — Medium. Surface texture — Smooth. Surface appearance — Semi-glossy to dull.

*Petiole.*—Length — About 15.3 cm. Length of petiole compared to middle vein — Slightly shorter. Density of prostrate hairs on petiole — Sparse. Density of erect hairs on petiole — None. Anthocyanin coloration of petiole — Very strong.

*Buds.*—Bud fruitfulness — Basal: Mostly fruitful. Position of first fruitful shoot on previous season cane — $2^{nd}$ to $4^{th}$ node. Time of bud burst — Medium; Mar. 14, 2012.

Flowers:

*General.*—Flower sex — Hermaphrodite. Length of first inflorescence — Medium long; About 22.6 cm long by 9.6 cm wide. Position of first flowering and fruiting node — $4^{th}$ to $5^{th}$ node (current season growth). Number of inflorescence per flowering shoot — Up to 1. Time of bloom — Late as compared with similar varieties in the growing area of Delano, Calif. Date of full bloom — May 18, 2012.

Fruit:

*General.*—Ripening period — Late; Approximately Oct. 10, 2012. Use — Fresh market. Keeping quality — Excellent. Resistance to — Insects: Average typical of *Vitis vinifera* species. Diseases: Average typical of *Vitis vinifera* species. Refractometer test — Soluble solids: About 17.6 Brix. Brix/acid — About 50.3. % Titratable acidity — About 0.35 g/100 ml. Juice pH — About 4.0.

*Cluster.*—Mature cluster length (peduncle excluded) — About 32.9 cm. Mature cluster width — About 18.2 cm. Mature cluster weight — About 1088 g. Bunch density — Medium. Number of berries — About 214. Form — Long Conical.

*Peduncle.*—Lignification of peduncle — medium. Length of peduncle — Medium long; Approximately 5.9 cm.

*Berry.*—Uniformity of size — Uniform. Single berry weight — About 7.8 g natural. Shape — narrow elliptic. Seeds — Contains small rudimentary seed traces which are not noticeable. Cross section — Circular. Berry dimensions — longitudinal axis: About 2.8 cm. horizontal axis: About 1.9 cm. Berry firmness — Firm. Particular flavor — Neutral. Bloom (cuticular wax) — Medium. Berry separation from pedicel — Medium to easy. Skin color (without bloom) — Greyed-Purple; about N186A.

*Skin.*—Thickness — Medium. Texture. — Medium. Reticulation — Absent. Tenacity — Tenacious to flesh.

What is claimed:

1. A new and distinct variety of grapevine as herein illustrated and described.

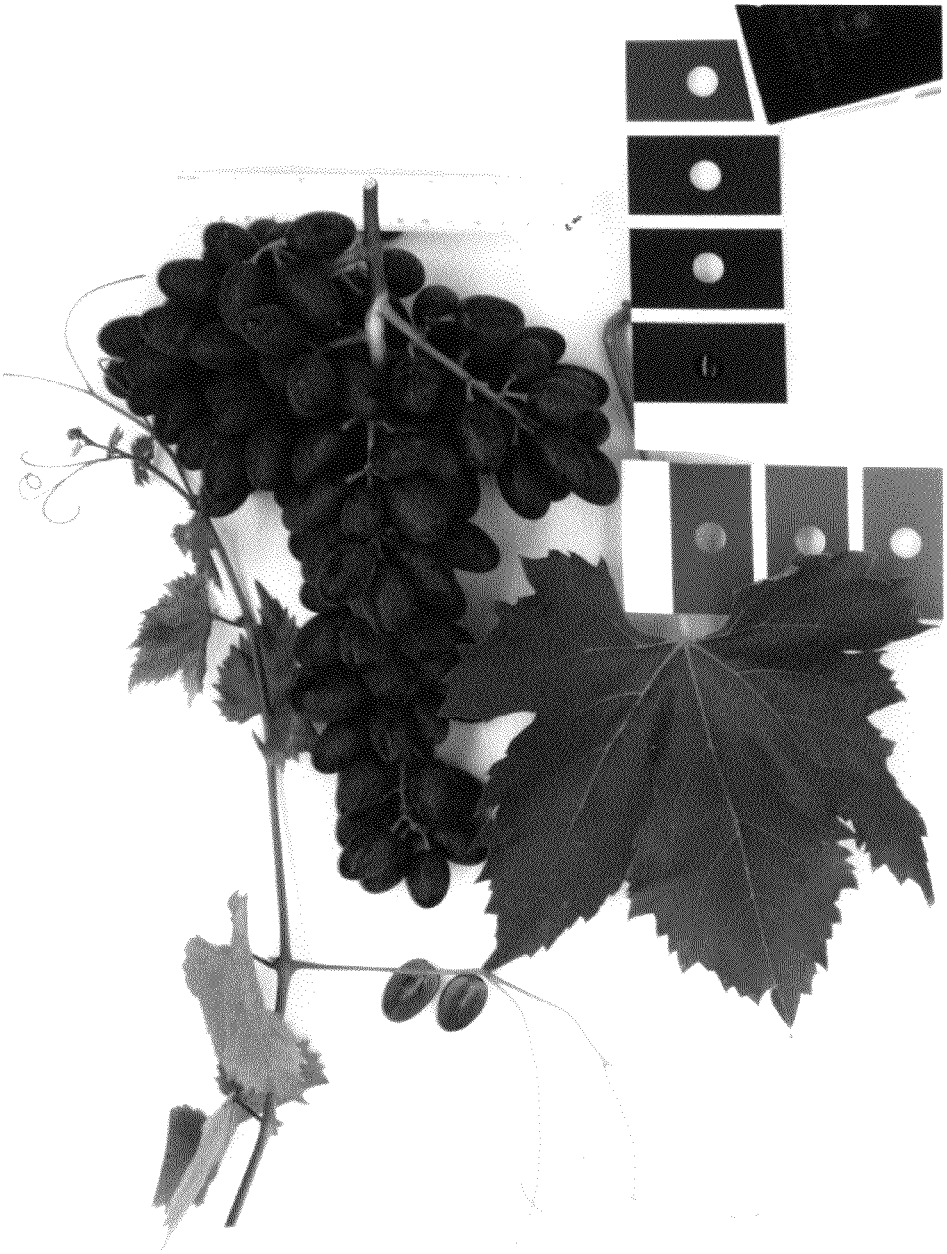

* * * * *